United States Patent [19]

Howse

[11] Patent Number: 4,820,513
[45] Date of Patent: Apr. 11, 1989

[54] INSECT ATTRACTANT

[75] Inventor: Philip E. Howse, Southampton, England

[73] Assignee: University of Southampton, Southampton, United Kingdom

[21] Appl. No.: 911,265

[22] Filed: Jul. 29, 1986

[30] Foreign Application Priority Data

Aug. 2, 1985 [GB] United Kingdom ............ 8519540

[51] Int. Cl.$^4$ ............................................ A01N 25/00
[52] U.S. Cl. ................................................. 424/84
[58] Field of Search ........................................ 424/84

[56] References Cited

U.S. PATENT DOCUMENTS 4,600,581 7/1986 Aldrich ............................ 424/84

OTHER PUBLICATIONS

*Advances in Pest Control Research*, vol. 8, p. 88 (1968).
Qureshi et al., Pakistan J. Sci. Ind. Res., vol. 19, No. 1, Feb., 1976.
Chemical Abstracts 89: 39687s (1978).
Controlled Release Technologies: Methods, Theory, and Applications, vol. 1, Chapter I, pp. 1-19 and title page (1978).
Insect Suppression with Controlled Release Pheromone Systems, vol. I, pp. 202-203, title page and Table 1 (1971).
Chemical Abstracts, vol. 92 (1980) 212122r "The pheromone bouquet of Ips amitinus".
Chemical Abstracts, vol. 95 (1981) 39380k "Pheromonal cues direct mate-seeking behavior of male Colletes cunicularius".
"Pheromone Communication in the Mediterranean Fruit Fly (Ceratitis capitata Weid.)", 1986, P. E. Howse and M. E. Foda, Biology Department, University of Southampton, U.K.
Isolation and Identification of the Sex Pheromone of the Mediterranean Fruit Fly, Ceratitis capitata (Wied), Baker, Herbert and Grant, TS-58590-C3-11:-31-29/4/85, Chemical Communications-Batch 79.
K. F. Haynes, "Insect Pheromones" The Institute of Biology's Studies in Biology No. 147, pp. 1-5 (1978).
Morris Rockstein, "Biochemistry of Insects", pp. 365-367 (1978).

*Primary Examiner*—Leonard Schenkman
*Attorney, Agent, or Firm*—Flynn, Thiel, Boutell & Tanis

[57] ABSTRACT

An insect attractant for the control of fruit flies comprises linalool together with an upwind flight stimulant. Preferably, the attractant is in a slow release formulation.

17 Claims, No Drawings

INSECT ATTRACTANT

This invention relates to insect attractant and to methods of preparing and using the attractant. The attractant is particularly useful in the control of populations of fruit flies of the family Trypetidae, which includes the mediterranean fruit fly *Ceratitis capitata*, the oriental fruit fly, *Dacus dorsalis*, the melon fly, *Dacus cucurbitae* and the Mexican fruit fly, *Anastrepha ludens*.

In the control of insect pests such as fruit flies it has been proposed to use pheromones, which influence the behaviour of the insects. For example, some pheromone components stimulate the insects to fly upwind and some stimulate the insects to land at the source of the pheromone. It has been observed heretofore that pheromones are sex specific.

It has now been found that the compound 3,7 dimethyl-1,6-octadiene-3-ol, linalool (or linalol) is an extremely powerful short range attractant which draws both male and female fruit flies of the family Trypetidae, and in particular mediterranean and oriental fruit flies, to the source of the attractant and arrests them there. Thus, the linalool acts not merely as a pheromone, which is effective for intraspecific communications, but as an allomone, which is effective for interspecific communication.

The present invention thus provides an insect attractant comprising linalool and an upwind flight stimulant for the insect to be attracted. It also provides a slow release insect attractant including a composition comprising linalool.

In a second aspect of the invention, a method of controlling the number of flies of the family Trypetidae, such as *Ceratitus capitata* and *Dacus dorsalis*, in a population comprises contacting at least part of the population with an insect attractant of the type provided by the first aspect of the invention. Further, the invention provides a method of preparing an insect attractant comprising mixing linalool with an upwind flight stimulant.

The effect of insect attractants according to the invention containing linalool is: (i) to activate the insect; (ii) to stimulate upwind flight by the insect; (iii) to stimulate the insects to land at the source of the insect attractant; and (iv) to arrest the insects at the source of the attractant.

The action stimulated by the insect attractants of the invention appears similar to that observed under natural conditions when male mediterranean fruit flies are attracted to each other to form groups known as leks. Female fruit flies are themselves attracted to the leks formed by the congregating males.

It is preferred that the insect attractants of the invention contain, in addition to linalool, an upwind flight stimulant. This has the desirable effect of encouraging the fruit flies to fly toward the source of the attractant, where they are encouraged to remain under the effect of the linalool in the attractant. Preferred upwind flight stimulants are: ethyl palmitoleate; trimedlure (a commercial attractant comprising t-butyl esters of 6-methyl-3-cyclohexenecarboxylic acids), geranyl acetate; 2,5-dimethyl pyrazine; 2,3-dimethyl pyrazine; E-2-hexenoic acid; furfuryl alcohol; E,E-α-farnesene; methyl eugenol.

It is further preferred that, in use, the linalool, preferably together with an upwind flight stimulant, be incorporated in a suitable slow-release medium, for example, rubber, polythene, hollow fibres, plastic sandwiches or membranes, or cellulosic materials, so that the attractant is released over a period of days or weeks at a concentration that would be adequate to attract male mediterranean fruit flies. Preferred dosages per lure are in the range 1 μl–100 μl.

The attractant may also be incorporated, together with insecticides, into baits which are sprayed to form droplets in the environments in which the insects occur, providing a lure and kill effect.

The attractant can also be used for mass trapping of fruit flies for example in known trap structures, in an attempt to achieve population reduction, or as a means for confusing the orientation of males so that they cannot aggregate in the normal way in the environment, or of females so that they cannot find males.

A further application of the attractants of the invention is in the detection of flies and in population monitoring.

EXAMPLES AND COMPARATIVE TESTS

In the following Examples, the lures comprise the attractant on a cellulose cigarette filter. Example 1, the control, was a blank cellulose cigarette filter. In all the Examples, the mediterranean fruit flies were released down wind of the lure.

Examples 2, 9 and 10 are of known flight stimulants, containing no linalool. The "% attracted" is the percentage of mediterranean fruit flies (from a sample of between 40 and 60 in the case of the male flies and 30 in the case of the virgin female flies) landing within a 5 cm radius of the lure within twenty minutes, in a 1.5 m × 0.5 m wind tunnel.

| EXAMPLES | SEX OF FLY | COMPOSITION | % ATTRACTED |
|---|---|---|---|
| 1 | M | Control | 3 |
| 2 | M | 5 μl Trimedlure | 30 |
| 3 | M | 5 μl linalool | 83 |
| 4 | M | 5 μl linalool | |
| | | 1 μl ethyl palmitoleate | 61 |
| 5 | M | 5 μl linalool | 80 |
| | | 1 μl E,E—α-farnesene | |
| 6 | M | 5 μl linalool | |
| | | 10 μl furfuryl alcohol | 78 |
| 7 | M | 5 μl linalool | |
| | | 5 μl geranyl acetate | 70 |
| 8 | M | 5 μl linalool | 83 |
| | | 1 μl 2,5-dimethyl pyrazine | |
| 9 | virgin F | 1 μl ethyl palmitoleate | 37 |
| 10 | virgin F | 5 μl hexenoic acid | 40 |
| 11 | virgin F | 10 μl linalool | 77 |

It should be noted that the linalool employed in the above Examples is a racemic mixture. It is to be expected that naturally occurring linalool is produced only as a single, active, optical isomer.

I claim:

1. In a method for attracting fruit flies of the family Trypetidae to a particular location, the improvement comprising:
   (1) placing at said location a lure containing an effective attractant composition consisting essentially of linalool and an upwind flight stimulant for said fruit flies, said location being upwind of said fruit flies;
   (2) stimulating upwind flight of said fruit flies; and (3) stimulating said fruit flies to land and remain at said location of said lure.

2. The method according to claim 1 in which said lure is a controlled release medium.

3. The method according to claim 2 in which the linalool and upwind flight stimulant composition is disposed on or in a controlled release medium selected from the group consisting of rubber, polythene, hollow fibres, plastic sandwiches, plastic membranes and cellulosic materials, so that the attractant is released over a period of days at a concentration effective to attract said flies.

4. The method according to claim 1 in which said attractant composition is contained in said lure in an amount of 1 microliter to 100 microliters.

5. The method according to claim 1 in which the upwind flight stimulant is selected from the group consisting of ethyl palmitoleate; t-butyl esters of 6-methyl-3-cyclohexenecarboxylic acids; geranyl acetate; 2,5-dimethyl pyrazine; 2,3-dimethyl pyrazine; E-2 hexenoic acid; furfuryl alcohol; E,E-α-farnesene and methyl eugenol.

6. The method according to claim 1 or claim 5, further comprising the step of contacting said fruit flies with an insecticide.

7. A method according to claim 1 in which the flies are *Ceratitis capitata* or *Dacus dorsalis*.

8. A method according to claim 1 in which the upwind flight stimulant is selected from the group consisting of ethyl palmitoleate, E,E-α-farnesene, furfuryl alcohol, geranyl acetate and 2,5-dimethyl pyrazine.

9. In a method of controlling the number of fruit flies of the family Trypetidae, the improvement comprising:
   (1) incorporating an attractant consisting essentially of linalool and an upwind flight stimulant for said fruit flies and an insecticide into a bait;
   (2) spraying said bait in an environment in which the fruit flies occur; and thereby
   (3) luring and killing said fruit flies in said environment.

10. The method of claim 9 in which said upwind flight stimulant is selected from the group consisting of ethyl palmitoleate; t-butyl esters of 6-methyl-3-cyclohexene carboxylic acids; geranyl acetate; 2,5-dimethyl pyrazine; 2,3-dimethyl pyrazine; E-2 hexenoic acid; furfuryl alcohol; E,E-α-farnesene and methyl eugenol.

11. In a method for controlling the number of fruit flies of the family Trypetidae in a population comprising said fruit flies, the improvement comprising contacting part of said population with an insect attractant consisting essentially of linalool and an upwind flight stimulant for said fruit flies.

12. The method of claim 11 in which said upwind flight stimulant is selected from the group consisting of ethyl palmitoleate; t-butyl esters of 6-methyl-3-cyclohexene carboxylic acids; geranyl acetate; 2,5-dimethyl pyrazine; 2,3-dimethyl pyrazine; E-2 hexenoic acid; furfuryl alcohol; E,E-α-farnesene and methyl eugenol.

13. In a method of attracting both male and female fruit flies of the family Trypetidae, the improvement comprising contacting said fruit flies with an attractant comprising linalool.

14. A method according to claim 13 in which said attractant further comprises an upwind flight stimulant.

15. A method of preparing an insect attractant for flies of the family Trypetidae comprising incorporating in a controlled release medium an attractant composition comprising linalool and an upwind flight stimulant, said medium being effective to release said attractant composition over a period of days at a concentration effective to attract said flies.

16. A method according to claim 15 in which the upwind flight stimulant is selected from the group consisting of ethyl palmitoleate; t-butyl esters of 6-methyl-3-cyclohexenecarboxylic acids; geranyl acetate; 2,5-dimethyl pyrazine; 2,3-dimethyl pyrazine; E-2 hexenoic acid; furfuryl alcohol; E,E-α-farnesene and methyl eugenol.

17. A method according to claim 15 in which the upwind flight stimulant is selected from the group consisting of ethyl palmitoleate, E,E-α-farnesene, furfuryl alcohol, geranyl acetate and 2,5-dimethyl pyrazine.

* * * * *